US00PP19209P2

(12) United States Plant Patent
Lamb et al.

(10) Patent No.: US PP19,209 P2
(45) Date of Patent: Sep. 9, 2008

(54) ***SPATHIPHYLLUM* PLANT NAMED 'SP9028-9'**

(50) Latin Name: *Spathiphyllum*
Varietal Denomination: SP9028-9

(75) Inventors: Ann Elizabeth Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/788,189

(22) Filed: Apr. 19, 2007

(51) Int. Cl.
*A01H 5/00* (2006.01)

(52) U.S. Cl. ..... Plt./364
(58) Field of Classification Search ..... Plt./364
See application file for complete search history.

*Primary Examiner*—Annette H Para
(74) *Attorney, Agent, or Firm*—Jondle & Associates, P.C.

(57) ABSTRACT

A new *Spathiphyllum* plant particularly distinguished by attractive, very highly branched, leafy growth habit, many relatively small, very dark green, shiny, textured leaves, abundant white ovate spathes with early natural bloom and tolerance of environmental extremes which often cause leaf yellowing in the other *Spathiphyllum* varieties is disclosed.

3 Drawing Sheets

Genus and species: *Spathiphyllum* hybrid.
Variety denomination: 'SP9028-9'.

BACKGROUND OF THE NEW PLANT

The present invention comprises a new and distinct cultivar of *Spathiphyllum,* botanically known as *Spathiphyllum* hybrid, and hereinafter referred to by the cultivar name 'SP9028-9'. The new cultivar originated from a hybridization made in June, 2002 in Apopka, Fla. The female parent with *Spathiphyllum* cv. 'Valentino' (U.S. Plant Pat. No. 13,670). The male parent was *Spathiphyllum* cv. 'Double Take' (U.S. Plant Pat. No. 12,835).

A single plant selection was chosen for further evaluation and for asexual propagation in March, 2004.

The new cultivar was first propagated in March, 2004 in Apopka, Fla. and has been asexually reproduced repeatedly by tissue culture in Apopka, Fla. over six generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Attractive, very highly branched, leafy growth habit;
2. Many relatively small, very dark green, shiny, textured leaves;
3. Abundant white ovate spathes with early natural bloom; and
4. Tolerant of environmental extremes which often cause leaf yellowing in other *Spathiphyllum* varieties.

DESCRIPTION OF PHOTOGRAPHS

This new *Spathiphyllum* plant is illustrated by the accompanying photographs which show overall plant habit including blooms, buds, and foliage of the plant; the colors shown are as true as can be reasonably obtained by conventional photographic procedures.

DESCRIPTION OF THE NEW CULTIVAR

Figure 1:
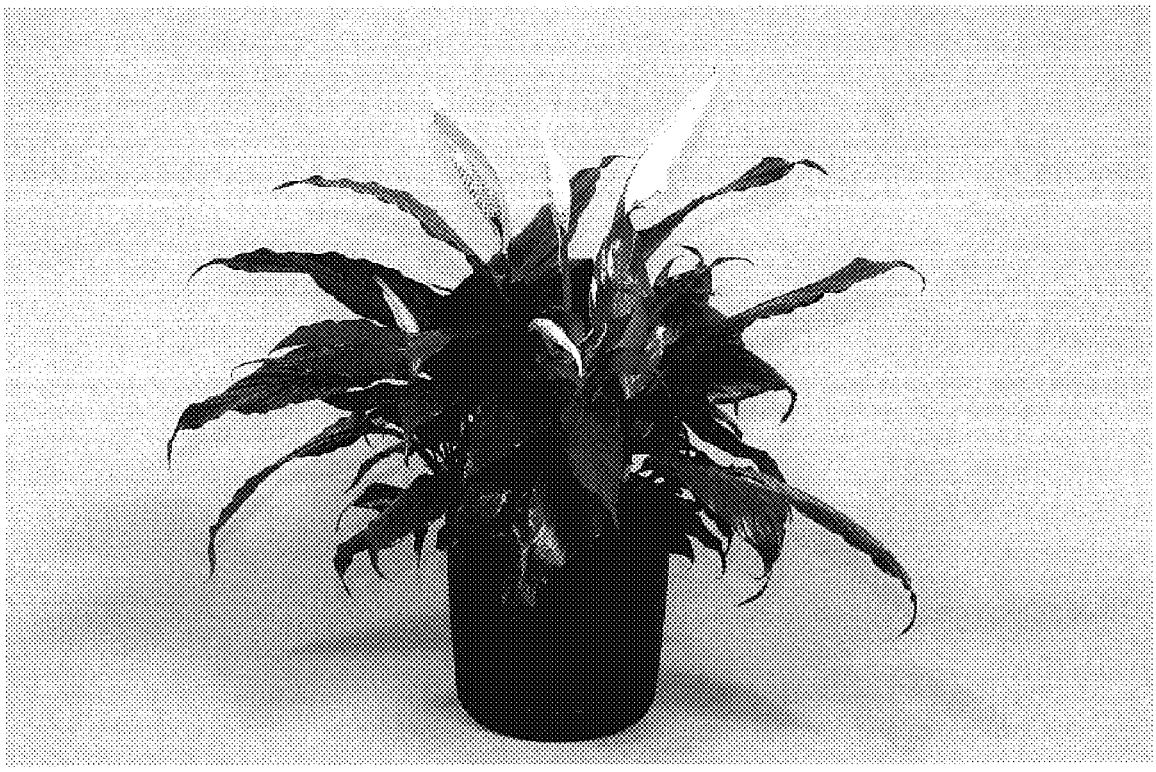
FIG. 1 shows the overall plant habit, including blooms, buds, mature foliage, and plant habit.
Figure 2:
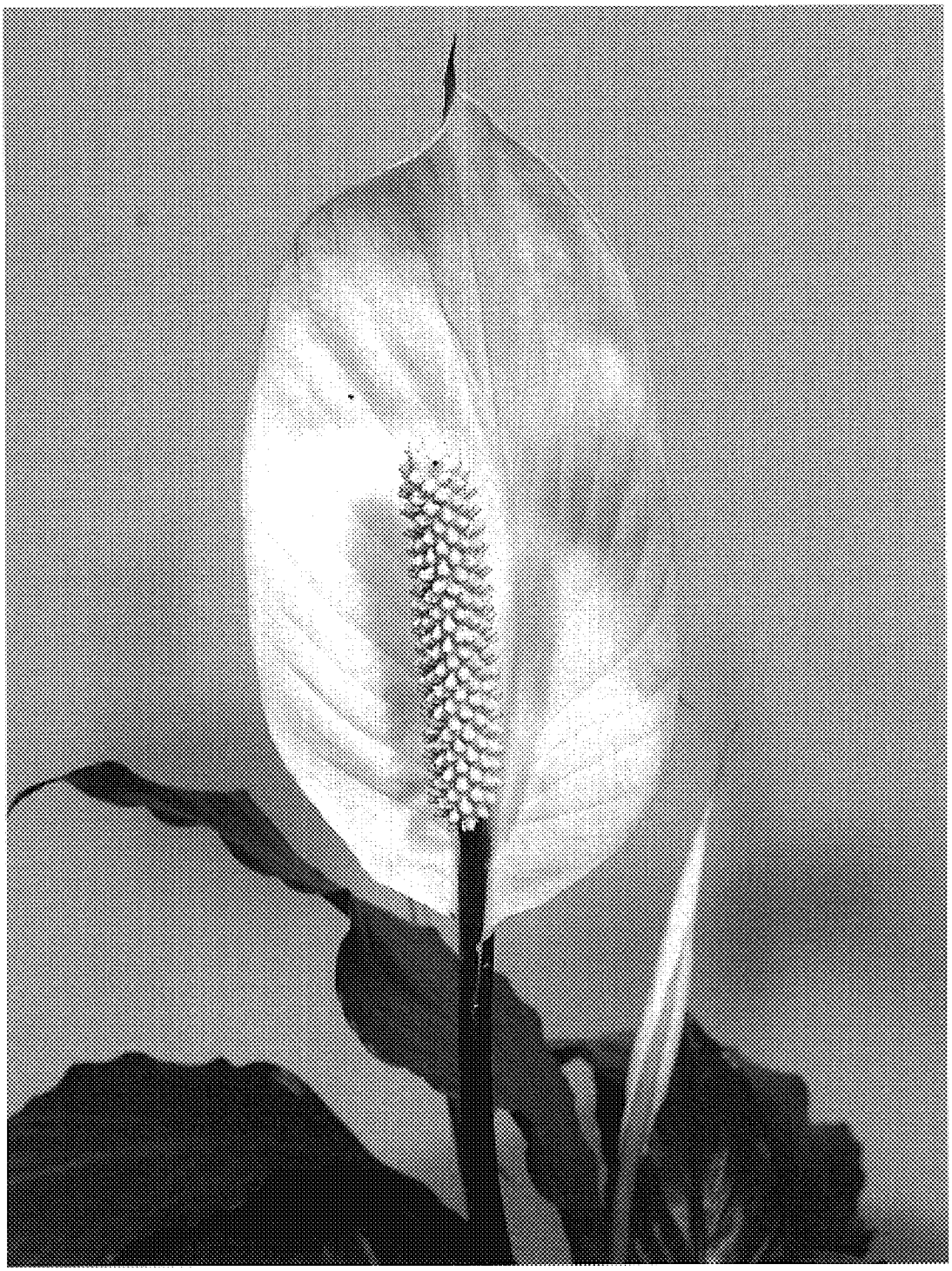
FIG. 2 shows a close-up of a mature inflorescence.
Figure 3:
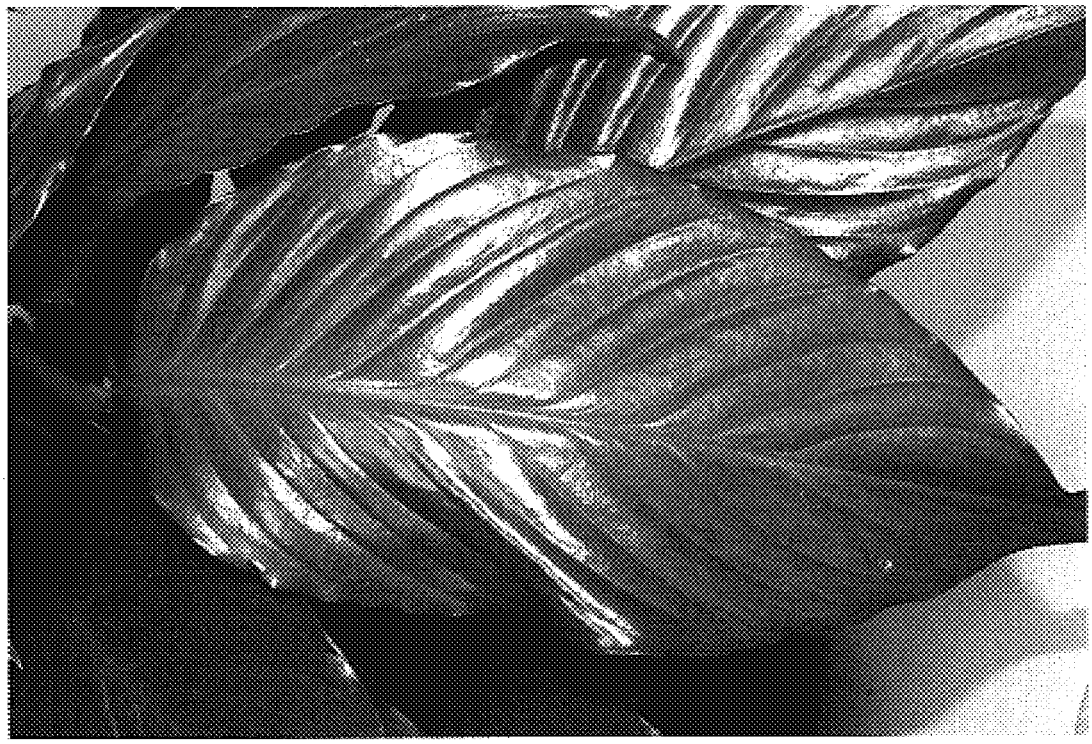
FIG. 3 shows the upper surface of a mature leaf.
Figure 4:
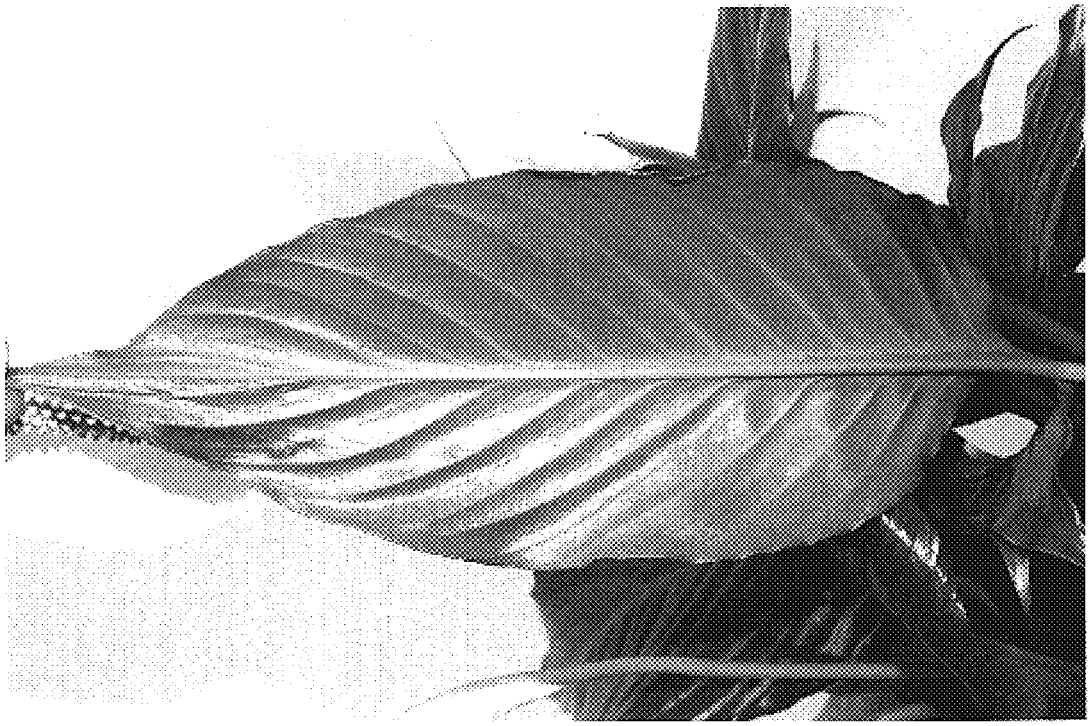
FIG. 4 shows the lower surface of a mature leaf.

The following detailed description sets forth the distinctive characteristics of 'SP9028-9'. The data which define these characteristics were collected from asexual reproductions carried out in Apopka, Fla. The data were obtained in April 2006 from 7-month-old plants grown in 15-cm pots and started from a 70- to 84-day-old liner initiated from a single tissue culture-derived micro-cutting. The plants were grown in a shade-cloth enclosure with a daily temperature range of 75 to 90° F. and a nightly temperature range of 65 to 72° F. The light level was about 2000 foot candles; there were no photoperiodic treatments or growth retardant treatments, however gibberellic acid was used to induce flowering. Color references are to the Royal Horticultural Society Colour Chart, 2001 edition.

DETAILED BOTANICAL DESCRIPTION OF THE NEW PLANT

Classification:
*Family.*—Araceae.
*Botanical name.*—*Spathiphyllum* hybrid.
*Common name.*—Peace lily, white anthurium.

Parentage:
*Female parent.*—*Spathiphyllum* cv. 'Valentino' (U.S. Plant Pat. No. 13,670).
*Male parent.*—*Spathiphyllum* cv. 'Double Take' (U.S. Plant Pat. No. 12,835).

Growth:
*General.*—Tropical flowering potted plant; plant is suitable for use in shaded tropical landscapes and in indoors.

*Time to finish.*—About 7 to 8 months to finish when starting from a 70- to 84-day-old liner initiated from a single tissue culture-derived micro-cutting.

*Appropriate container.*—10 cm to 15 cm pots; suitable for use in shaded tropical landscapes and indoors.

Plant description:

*Life cycle.*—Herbaceous perennial.

*Habit.*—Upright symmetrical shape; leaves upright when juvenile, arching outward as the plant matures.

*Height, from soil to top of leaf plane.*—22.0 cm to 28.0 cm.

*Height, from soil to top of inflorescences.*—34.0 cm to 38.0 cm.

*Spread.*—43.0 cm to 48.0 cm.

*Vigor.*—Good.

*Roots.*—Thick, fleshy, white, freely branching with fine lateral branches.

*Durability of foliage to stresses.*—Better than average durability when grown indoors; good tolerance to mechanical damage from shipping and handling.

*Temperature tolerances.*—Tolerates high temperatures to about 104° F. and low temperatures to about 45° F. without noticeable damage.

Stems:

*Type.*—Basal branching.

*Number.*—16 basal branches originating from a single micro-cutting.

*Description.*—Ovate to columnar, round in transverse section.

*Length.*—1.5 cm to 2.5 cm depending upon age of shoot.

*Diameter.*—1.0 cm to 2.3 cm depending upon age of shoot.

*Internode length.*—0.4 cm.

*Aspect.*—Upright.

*Strength.*—Tough, somewhat flexible.

*Color.*—Immature: Outside: RHS 155C (white). Inside: RHS 155C (white). Mature: Outside: RHS 155C (white) tinged with RHS 137B to RHS 137C (green) if exposed to light. Inside: RHS 155C (white).

Leaves:

*Arrangement.*—Alternate, simple; leaves arranged on stem in closely spaced vertical ranks.

*Number.*—6 to 8 leaves per stem; fewer on younger shoots.

*Shape.*—Lanceolate.

*Apex.*—Acuminate.

*Base.*—Obtuse to cuneate.

*Margin.*—Entire, wavy.

*Size.*—Length: 18.0 cm to 21.0 cm. Width: 6.5 cm to 8.0 cm.

*Color.*—Immature leaf: Upper surface: Greener than, but closest to RHS 137A. Lower surface: RHS 147B. Mature leaf: Upper surface: Much darker and greener than, but closest to RHS 147A. Lower surface: RHS 137B.

*Venation.*—Type: Pinnate; main veins and mid-rib recessed on upper surface and protruding from lower leaf surface.

*Color.*—Upper surface: Much darker and greener than, but closest to RHS 147A. Lower surface: RHS 146B to RHS 147B.

*Texture.*—Upper surface: Smooth, shiny; blade convex between main veins giving the leaf a textured appearance. Lower surface: Smooth, glossy.

*Surface pubescence.*—Absent.

Petiole:

*Length.*—15 cm.

*Diameter, distal.*—0.45 cm.

*Diameter, proximal* (*flattened for measurement*).—4 cm; base of petiole clasps and encircles the stem.

*Aspect.*—Upright when newly emerged becoming about 45 degrees from the vertical axis as more leaves emerge above it.

*Color.*—Much darker and greener than, but closest to RHS 147A.

Geniculum:

*Length.*—3.0 cm.

*Diameter.*—0.45 cm.

*Aspect.*—Curved outward.

*Color.*—Darker and greener than, but closest to RHS 147A.

*Wing length* (*petiole sheath*).—10.0 cm to 12.0 cm.

*Wing diameter.*—0.8 cm at midpoint.

*Wing color.*—Darker and greener than, but closest to RHS 147A.

Peduncle:

*Length, as measured from base of peduncle to base of spathe.*—18.0 cm to 25.0 cm.

*Diameter.*—0.3 cm to 0.4 cm.

*Angle.*—Straight, upright.

*Strength.*—Touch, flexible.

*Color.*—RHS 137A to RHS 147A.

Inflorescence:

*Arrangement.*—Cupped, ovate flower spathe surrounding a columnar spadix borne atop a tall upright peduncle; monoecious; spadix a central column of densely packed, sessile, simple flowers.

*Flowering habit.*—Natural bloom starts in the late winter and repeat flowering occurs for about 3 to 4 months; flowering can be induced by applying gibberellic acid at any time of the year.

*Lastingness of the spathes on the plant.*—About 3 to 4 weeks with good color; spathes become tinged with green as they age; senescence/browning occurs after about 8 to 10 weeks.

*Longevity as a cut flower.*—About 7 days.

*Persistent/Self-cleaning.*—Persistent.

*Flowering season.*—Late winter through summer.

*Time to flower.*—Inflorescences initiated about 12 weeks after induction.

*Rate of inflorescence opening.*—About 2 to 3 new inflorescences open every 7 to 10 days.

*Number of inflorescences per plant.*—About 15.

*Fragrance.*—Sweet perfume.

*Inflorescence height.*—34.0 cm to 38.0 cm.

*Immature inflorescence* ("*bud*").—Spathe tightly rolled around spadix. Shape: Spindle-shaped. Length: About 5.5 cm. Width: 1.0 cm. Color: Whiter than, but closest to RHS 155A; mid-rib RHS 143A; apex tinged with RHS 143A.

Spathe:

*Arrangement.*—Straight, upright.

*Shape.*—Ovate, cupped.

*Margin.*—Entire.

*Apex.*—Acuminate.

*Base.*—Cuneate to obtuse.

*Length.*—10 cm to 12 cm.

*Diameter.*—4.5 cm to 6 cm.

*Height* (*depth*).—2.5 cm.

*Texture.*—Both sides smooth, slightly glossy.

*Color, when opening.*—Front side: RHS 155D; apex tinged with RHS 143A. Rear side: Whiter than but closest to RHS 155A; mid-rib RHS 143A; apex tinged with RHS 143A.

*Color, when fully opened.*—Front side: Paper white; apex tinged with RHS 143A. Rear side: paper white; mid-rib RHS 143A; apex tinged with RHS 143A.

*Color, fading to.*—After about 3 to 4 weeks, spathes become progressively more tinged with RHS 143A to RHS 143B (green) as they age, ultimately becoming RHS N199B with senescence.

Spadix:

*Arrangement.*—Straight, upright.

*Shape.*—Columnar.

*Margin.*—Spadix covered with cone-shaped flower pistils.

*Apex.*—Blunt, rounded.

*Base.*—Obtuse.

*Length.*—4.4 cm to 5.3 cm.

*Diameter.*—1.5 cm.

*Color.*—Immature: RHS 150D. Mature: RHS 158D.

*Flowers.*—Type: Simple, individual flowers reduced to the most basic elements. Shape: Elliptic to ovate, with protruding cone-shaped pistil surrounded by four tepals. Flower diameter: 0.3 cm. Flower height (depth): 0.5 cm to 0.6 cm overall from base to tip; cone-shaped pistil extends about 0.3 cm beyond the male flowers. Number of female flowers per spadix: 80 to 105. Number of male flowers per spadix: 8.

Reproductive organs:

*Stamens.*—Quantity: 8. Anther length: 0.2 cm to 0.3 cm. Anther color: RHS 158D. Pollen amount: Moderate to abundant. Pollen color: RHS 155D.

*Pistils: Quantity:* 80 to 105. Length: 0.5 cm to 0.6 cm. Pistil shape: Cone-shaped. Stigma color: RHS 158D. Ovary color: RHS 158D.

Fruit and seed set: Has not been observed.

Disease and insect resistance: Resistance and susceptibility is typical of the species.

COMPARISON WITH PARENTAL AND COMMERCIAL CULTIVARS

'SP9028-9' differs from the female parent *Spathiphyllum* 'Valentino' (U.S. Plant Pat. No. 13,670) in that 'SP9028-9' has a shorter and narrower plant habit than 'Valentino'. In addition, 'SP9028-9' has a longer and wider spadix and longer pistillate flowers than 'Valentino'.

'SP9028-9' differs from the male parent *Spathiphyllum* 'Double Take' (U.S. Plant Pat. No. 12,835) in that 'SP9028-9' has a less upright and shorter plant habit than 'Double Take'. Additionally, 'SP9028-9' has shorter narrower leaves and shorter narrower peduncles than 'Double Take'.

'SP9028-9' differs from the commercial *Spathiphyllum* variety '31581' (U.S. Plant Pat. No. 10,893) in that 'SP9028-9' has a more branched and denser, leafy habit than '31581'. In addition, 'SP9028-9' has smaller more textured leaves and an early prolific natural bloom when compared to '31581'.

I claim:

1. A new and distinct cultivar of *Spathiphyllum* plant as shown and described herein.

* * * * *